US007505917B2

(12) United States Patent
Howe et al.

(10) Patent No.: US 7,505,917 B2
(45) Date of Patent: Mar. 17, 2009

(54) METHOD FOR IMPROVING PHARMACEUTICAL SELECTION RATIOS IN PHARMACY IMPLEMENTATION OF PRESCRIPTION MEDICATION DISPENSING PLANS

(75) Inventors: Frederick Howe, La Jolla, CA (US); William J. Barre, Escondido, CA (US); Michael W. Lyon, Olivenhain, CA (US)

(73) Assignee: Medimpact Healthcare Systems, Inc., San Diego, CA (US)

( * ) Notice: Subject to any disclaimer, the term of this patent is extended or adjusted under 35 U.S.C. 154(b) by 253 days.

(21) Appl. No.: 11/397,928

(22) Filed: Apr. 4, 2006

(65) Prior Publication Data

US 2007/0233516 A1 Oct. 4, 2007

(51) Int. Cl.
*G06Q 10/00* (2006.01)
(52) U.S. Cl. .............................................. 705/2; 705/3
(58) Field of Classification Search ...................... 705/2
See application file for complete search history.

(56) References Cited

U.S. PATENT DOCUMENTS 6,195,612 B1 * 2/2001 Pack-Harris .................... 702/2
2006/0271402 A1 * 11/2006 Rowe et al. .................... 705/2

* cited by examiner

*Primary Examiner*—C Luke Gilligan
*Assistant Examiner*—Neal R Sereboff
(74) *Attorney, Agent, or Firm*—Gordon & Rees, LLP

(57) ABSTRACT

A method is disclosed by which pharmacies and physicians are encouraged to select appropriate and effective medications but dissuaded from selecting higher priced medications where more economical versions are available as alternatives, but where physicians and patients can also select such higher priced medications if they so choose and are prepared to pay that higher price. Under this system a single representative price (capitation rate) is calculated by a prescription payment plan manager for a group of related medications, usually including both branded and generic, and that price is paid to a pharmacy for all prescriptions of that group of medications fulfilled under the plan. The representative prices for different groups, including their minimum levels, are periodically reviewed and updated as appropriate.

12 Claims, 1 Drawing Sheet

METHOD FOR IMPROVING PHARMACEUTICAL SELECTION RATIOS IN PHARMACY IMPLEMENTATION OF PRESCRIPTION MEDICATION DISPENSING PLANS

FIELD OF THE INVENTION

The present invention relates generally to the field of filling prescriptions for consumers. More particularly it relates to prescription payment benefits made available by health plans, employer groups, governmental entities and other organizations to their employees and/or members.

BACKGROUND OF THE INVENTION

Many employees and members ("consumers") of health maintenance organizations, employer groups and government entities have their purchases of personal prescription medications subsidized by payments to pharmacies through prescription benefit plans ("plans") offered by those health maintenance organizations, employer groups and government entities. Under such plans, a consumer receives a prescription for a medication from his or her physician and submits it to a pharmacy to be filled. The pharmacy checks to see that the consumer is a member of a plan with which the pharmacy has a contract and that the medication and dosage prescribed are within the approved scope of the plan contract. Upon verification of these requirements, the pharmacy dispenses the medication to the consumer. The consumer pays the pharmacy a "copay" amount, less than the normal cost of the medication. The pharmacy receives the balance of the payment for the medication and its dispensing services from the prescription benefit plan, which is managed by a "prescription benefit manager" ("PBM") with whom the health maintenance organization, employer group or government entity ("payer") has contracted to manage the plan. The PBM invoices the payer (i.e., the PBM's customer) for the consumer's transaction, along with a charge for its contracted fee, and from the funds paid by the payer the PBM pays the pharmacy's balance due.

Conventionally brand name prescriptions are priced by starting with a nationally published "average wholesale price" (AWP) and discounting this figure. A dispensing fee is then added to this number. On the other hand, in the prior art systems generic drug claims usually employ an additional variant for pricing. This is a concept known as "maximum allowable cost" (MAC) pricing. MAC is the concept of paying a set price for a product on a per unit basis. Since multiple manufacturers may produce the same generic drug and dosage, the MAC price is applied regardless of the manufacturer or that particular manufacturer's AWP. It is common that prescriptions are paid at the lower of a) AWP minus a discount plus a dispensing fee or b) MAC plus a dispensing fee.

Because the cost of medications is so high and is such a large component of medical care costs generally, there is an on-going effort on the part of PBMs and payers to seek ways in which to control medication costs. Pharmaceutical medications are commonly available to consumers (patients) either in "brand name" (proprietary) or generic form. In some cases, especially for new or patented medications, only the brand name medication is available, usually only from a single source—the developer of the medication. For many others, however, there is no proprietary limitation on manufacture of the medication, and multiple sources of the medication—in generic or alternative brand name form—are available. Further, it is common that for a given class of pharmaceuticals, there are several different medications with substantially equivalent medical and physiological effects. Some of these medications may be proprietary brand name products while others may be generic and yet others may have been available in both generic and brand name forms. Retail prices charged by pharmacies can vary widely, especially where a particular medication is available in both brand name and generic form. Reimbursement rates paid to pharmacies vary depending on the product based on traditional reimbursement methodologies.

Physicians and other health care providers who write prescriptions therefore often have choices among the different medications they can prescribed for a patient. A physician can, for instance, prescribe a brand name medication or a generic form of that medication, or he/she can choose between two or more different but equivalent medication compositions. If the physician prescribes a brand name medication, he/she can also designate whether a dispensing pharmacy must dispense only that specific medication or can substitute an equivalent generic medication. There are of course significant differences in retail cost among the different medication forms, with generic forms normally being substantially lower in cost than brand name medications. However, either within each group (brand name or generic) there can be substantial cost differences, depending usually on the wholesale prices set by the various manufacturers. Thus for a single therapeutic category a physician, pharmacy and patient may be faced with numerous forms of the same or equivalent medications, all with different pricing.

PBMs are effectively in the middle of the prescription/pricing system, acting to obtain the most economical pharmaceutical prices for their clients, the payers, while at the same time seeking to insure that the pharmacies with which they contract for prescription fulfillment remain stable, economically viable and efficient businesses. Therefore it is valuable to all concerned—pharmacies, PBMs, payers and patients—for there to be a convenient, fair and effective system for managing medication costs under which patients can receive the medications they need at costs which are optimum for all. Such a system should provide a mechanism by which pharmacies and physicians are encouraged to select appropriate and effective medications but dissuaded from selecting higher priced medications where more economical versions are available as alternatives, but where physicians and patients can also select such higher priced medications if they so choose and are prepared to pay that higher price. It is a object of this invention to provide such a system.

SUMMARY OF THE INVENTION

The method of this invention is applicable to all types of prescriptions, including but not limited to those considered "short term", "acute care", "long-term" and "maintenance". It will be understood also that the method of the present invention is equally applicable to management of all prescription fulfillment and dispensing of medications in any dosages or quantities. Similarly, the particular total days' supply of a dispensing prescription, whether the exemplary and commonly used 30- and 90-day quantities, or 14-, 60-, 100-day or any other quantities, is to be understood to be within the scope of the invention. Those skilled in the art will be readily able to calculate and apply the appropriate discount and other payments for any desired dispensed quantity or medication.

The present invention provides an innovative system under which groups of medically similar medications are defined—e.g., lipotropics, antidepressants, oral contraceptives, non-steroidal anti-inflammatory drugs (NSAIDs), etc.—and an overall representative retail price of all of the medications in each group is calculated. Such calculations are normally made by determining the usual AWP/MAC prices, including discounts and dispensing fees, for each medication in the group—both brand name and generic products—and the percentage of the group sales each of the medications is responsible for over a specific time period. These "dispensed-weighted" prices for the various medications are then totaled and the total is designated as the representative price for the group as a whole. Typically where there are several brand name drugs and several generic drugs in the group with their different prices, the representative price will be an amount intermediate between the higher priced brand name product prices and the lower generic product prices. The "usual" reimbursement is based on what the payer is billed by the PBM.

Under this system the PBM agrees to pay a pharmacy the representative price for any and all of the group medications dispensed by that pharmacy. By using the representative price the PBM can also quote to its clients (the payers) subscription and management fees for administering the payers' pharmaceutical prescription plans which include effective cost control measures under this system. The pharmacy is then encouraged to use the lower priced medications where appropriate and possible, since the pharmacy earns (or loses) money in the amount which is the difference between the price it pays for the medication from the manufacturer or distributor and the representative price "fixed" fee that it receives from the PBM. Pharmacies are also thereby encouraged to request from physicians either directly or through their patients that the physicians where appropriate prescribe the lower priced medications or at least give the pharmacies the option of substituting such lower priced medications, to insure that the pharmacies will remain profitable. To insure that the representative price paid by the PBMs remains fair to both pharmacies and payers, the representative price calculations are done periodically, which may be on a weekly, biweekly, monthly or other basis, depending on the difference medication groups and how their dispensing rates and prices may fluctuate, and the representative prices for the various groups adjusted accordingly.

So far the description of the system has defined aspects which have been known and in commercial use for several years, although limited in actual practice. More recently, however, the need for improvement to enhance the system from both the pharmacies' and the payer's points of view has been recognized. Thus the present invention involves the basic system enhanced by differentiation of different types of medications within a group, multiple layers of representative price review, capitation and adjustment, and further incentive to pharmacies to seek the most economical medications consistent with good medical practice and physicians' instructions.

DETAILED DESCRIPTION OF THE INVENTION

Figure 1:
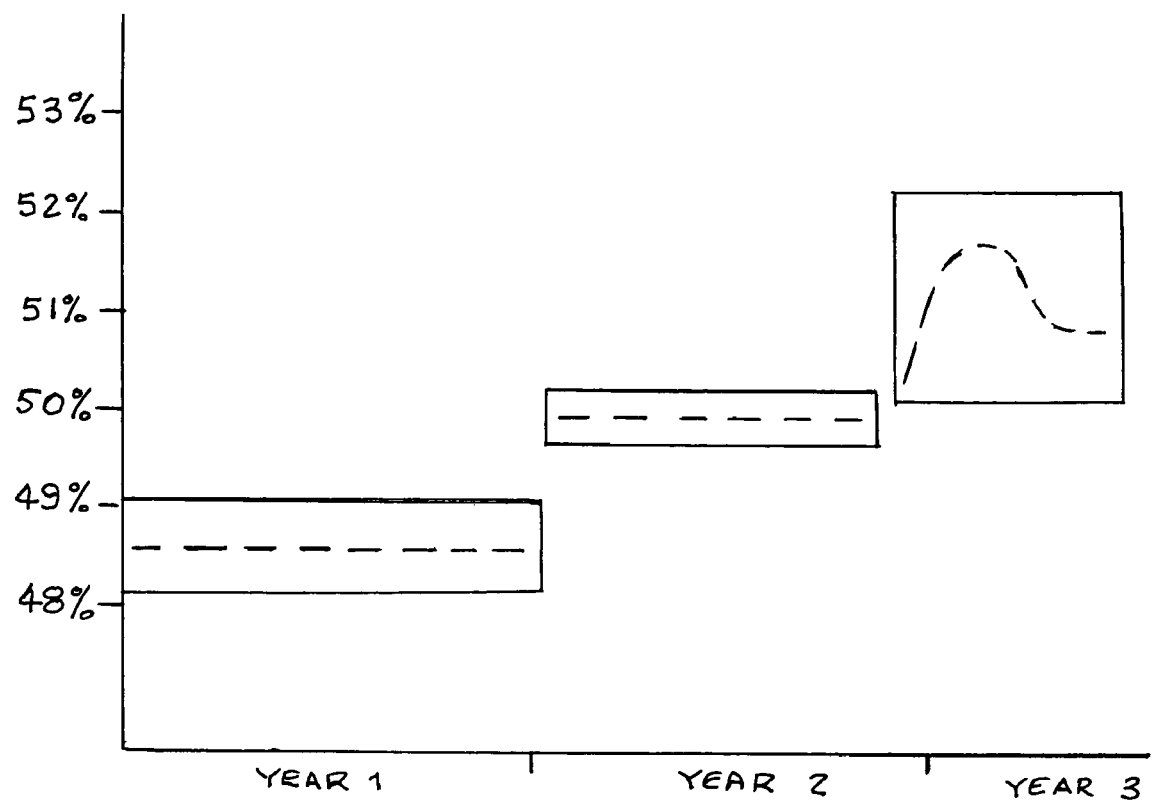
FIG. 1, the single FIGURE of the drawings, is a graph over time (>2 years) illustrating the increase in average percentage generic medication utilization involving the fixed fee payment system incorporated in this invention at a representative group of pharmacies. The boxes indicate the range of data fluctuations as measured at two-week intervals while the dashed line within each box indicates the overall trend of the data during the overall time period indicated by the box.

As noted above, the present invention provides an innovative system under which groups of medically similar medications are defined—e.g., lipotropics, antidepressants, oral contraceptives, non-steroidal anti-inflammatory drugs (NSAIDs), etc.—and an overall representative retail price of all of the medications in each group is calculated. Such calculations are normally made by determining the usual AWP/IMAC prices, including discounts and dispensing fees, for each medication in the group—both brand name and generic products—and the percentage of the group sales each of the medications is responsible for over a specific time period. These "dispensed-weighted" prices for the various medications are then totaled and the total is designated as the representative price for the group as a whole. Typically where there are several brand name drugs and several generic drugs in the group with their different prices, the representative price will be an amount intermediate between the higher priced brand name product prices and the lower generic product prices.

The calculation is illustrated in the Table that follows, which assumes an simulated medication group which includes brand name drugs A-E and generic drugs F-J, and up to 30-day prescription quantities for all. For each the AWP price, the AWP/MAC discount, the fill (dispensing) fee and the total retail cost are shown in columns 2-5. As noted, "AWP" means "average wholesale price" of a medication or medication group, whether brand name or generic, usually available from a single or limited number of producers, and is commonly a price determined on a national basis independently of the PBM, pharmacy or plan contracts. "MAC", also as noted, means "maximum allowable cost" of a generic medication, which usually is calculated from consideration of marketplace prices for the medication from different producers. Such pricing data are commercially and publicly available from various sources. Column 6 shows the percentage of the group dispensings which comprised the drug in question, followed by the percentage price contribution of the drug. At the bottom of column 7 of the table the individual price contributions are totaled yielding the representative price for the group as a whole. This is the "fixed fee" amount that the PBM then pays to the pharmacy for each dispensing of any medication in the group, regardless of whether it is a brand name drug or a generic drug.

TABLE 1

Calculation of Representative Price (Fixed Fee)

| Medication | AWP | AWP/MAC Discount | Fill Fee | Total Cost | Percent Dispensed | Percent Contribution |
|---|---|---|---|---|---|---|
| Drug E Brand | $92.00 | 15% | $2.50 | $80.70 | 6% | $ 4.84 |
| Drug B Brand | $84.00 | 15% | $2.50 | $73.90 | 5% | $ 3.70 |
| Drug D Brand | $76.00 | 15% | $2.50 | $67.10 | 3% | $ 2.01 |
| Drug A Brand | $75.00 | 15% | $2.50 | $66.25 | 20% | $13.25 |
| Drug C Brand | $63.00 | 15% | $2.50 | $56.05 | 16% | $ 8.97 |

TABLE 1-continued

Calculation of Representative Price (Fixed Fee)

| Medication | AWP | AWP/MAC Discount | Fill Fee | Total Cost | Percent Dispensed | Percent Contribution |
|---|---|---|---|---|---|---|
| Drug F Generic | $50.00 | 58% | $2.50 | $23.50 | 11% | $ 2.59 |
| Drug G Generic | $48.00 | 58% | $2.50 | $22.66 | 4% | $ 0.91 |
| Drug J Generic | $43.00 | 58% | $2.50 | $20.56 | 5% | $ 1.03 |
| Drug H Generic | $29.00 | 58% | $2.50 | $14.68 | 18% | $ 2.64 |
| Drug I Generic | $21.00 | 58% | $2.50 | $11.32 | 12% | $ 1.36 |
| Representative Price/Payment | | | | | | $41.29 |

It will be seen from the Table that the representative price falls generally midway between the brand name drug prices and the generic drug prices. In this simulated example the two classes of drugs are shown as each contributing 50% to the overall sales of this group of medications. If the ratio of class contributions to the group sales were in a ratio other than 50%-50%, the calculated representative price would be reflective of that ratio. Further, one or more drug prices significantly out of line with others in its class will also affect the representative price.

Under this system the PBM agrees to pay a pharmacy the representative price for any and all of the group medications dispensed by that pharmacy. It will be seen that a pharmacy selling this mix of drugs in this class will have a net deficit in the range of $14.79-$39.41 on sales of the brand name drugs. On the other hand, the pharmacy will have a net profit in the range of $17.79-$29.97 on sales of the generic drugs. Thus the pharmacy is encouraged to use the lower priced medications where appropriate and acceptable to the physician, since the pharmacy earns (or loses) money in the amount which is the difference between the price it pays for the medication from the manufacturer or distributor and the representative price "fixed" fee that it receives from the PBM. Pharmacies are also thereby encouraged to request from physicians either directly or through their patients that the physicians where appropriate prescribe the lower priced medications or at least give the pharmacies the option of substituting such lower priced medications, to insure that the pharmacies will remain profitable. To insure that the representative price paid by the PBMs remains fair to both pharmacies and payers, the representative price calculations are done periodically, which may be on a weekly, biweekly, monthly or other basis, depending on the different medication groups and how their dispensing rates and prices may fluctuate, and the representative prices for the various groups adjusted accordingly. By using the representative price the PBM can also quote to its clients (the payers) subscription and management fees for administering the payers' pharmaceutical prescription plans which include effective cost control measures under this system.

There have been, however, aspects of this system which have been found not to adequately reflect the interests of the PBMs, the payers or the pharmacies. It has been found that there are certain groups of medications whose prices are not equitably addressed by the basic system. A principal group to which this applies is those new medications released within the previous year, for which stable price levels are often not established for several months, and in particular which may command elevated prices for a period after introduction because of their novelty. It has been determined that this group of medications is not initially suitable for price support capitation, so they are excluded from the basic plan for the first twelve months from their date of introduction. Another class of medication for which capitation, or at least capitation at a standard calculated rate for related medications, is not applicable is those medications for which the AWP to the pharmacy exceeds $200. These medications have a price structure which is usually sufficiently far outside the normal range of related medications that to include them in the regular representative price calculation for their normal medication group would unduly skew the calculation and raise the representative price paid as a fixed fee by the PBMs to a level unrepresentative of the prices of the other members of the group, and thus represent a burden on the payers with respect to their plans' inclusion of the regular medications in that group. In both the new medication and the "$200+" medication, therefore, the present improvement invention excludes these from fixed fee/representative price calculations and instead substitutes a fee-for-service payment based on the individual medication's actual price. Thus the payer is still charged on a conventional billing basis as anticipated by the subscription contract with the PBM, which will include the fee-for-service payments for these medications, but which will not be distorted by them with respect to the other, regular medications and medication groups to which the regular fixed fee calculations pertain. On the other hand, the pharmacy is paid by the PBM on the fee-for-service basis rather than on the fixed fee basis for these special circumstance medications, which provides appropriate compensation to the pharmacy without providing a windfall with respect to the pharmacy's normal payments on the fixed fee, capitation basis.

It has also been found that capitation minimums must be considered and adjusted periodically. The capitation rate, i.e., the fixed fee, must not be allowed to be so low that the pharmacy has insufficient incentive to dispense lower cost medications as compared to higher cost ones. If the fee paid by the PBM for a medication group is too low, many pharmacies will not conclude that there is a significant difference between their costs and the fixed fee to create an adequate profit margin for them, and they will make no effort to substitute generic drugs for brand name ones, and they will simply pass on the cost differential on all of the medications to the patient. This of course will displease the patients and, through them, the payers. Thus the current invention enhances the basic system by including means to periodically assess capitation procedures and the calculated representative prices to determine if the fixed fees being paid to the pharmacies for the various medication groups are adequate to assure that the pharmacies see sufficient profit margin in the fixed-fee-paid generic drugs to encourage use of those in preference to the higher priced branded drugs. As an example, over time the AWPs for medications generally increase so that the AWPs for more individual medications reach or exceed $200, resulting in a decrease in the number of claims which are eligible for fixed fee payment. By increasing the representative price, say from $200 to $300, the AWPs of many of these medications again fall under the fixed fee calculation.

It will be recognized that a key element in the present invention is the means available to the PBMs to collect all of the data on pharmacy and medication pricing, analyze it in accordance with the pricing and dispensing characteristics of the various defined medication groups, thereafter determine the appropriate representative prices for each of those groups, and to repeat these steps periodically and frequently, as described above, to insure that all parties—the pharmacies, payers and patents—are provided with optimum levels of payment and plan support by the PBMs. Clearly the most practical manner of doing this is to incorporate the system into computer software which has the capability of storing all of the data, analyzing the data through the appropriate mathematical and statistical functions, and providing in a timely manner the pricing and capitation information that the PBM personnel need in order to manage the payers' plans in a satisfactory manner and maintain the participation interest of the pharmacies. The details of such software will be readily determined by those skilled in that art, and appropriate accounting, data analysis and statistical software programs are either commercially available or can be readily produced or adapted from commercial software. What is important to the present invention is not the particular programming code that a user might choose for a specific step, but rather that all of the different code units are assembled in the unique manner dictated by present invention and evident to those skilled in the art from the above description of the functions to be accomplished and the calculations to be performed. An example of such software is a program developed as part of the present invention and referred to as "Pharmacy Dashboard". This program enables the PBM to provide remote online access to participating pharmacies so that each pharmacy or pharmacy chain can assess and compare pharmacy performance over time under the present invention according to drug category, prescription dispensing date and/or store (for multi-store pharmacy groups or companies). A participating pharmacy or pharmacy group can determine either or both prescription profit sums and averages overall and/or separately for branded and generic drugs.

Although several embodiments of the invention have been described above by way of example only, it will be understood by those skilled in the field that numerous variations and modifications may be made to the disclosed embodiments without departing from the scope or spirit of the invention, as it is defined by the appended claims.

We claim:

1. A computer based method for improving pharmacy medication selection ratios in a prescription fulfillment plan which comprises:
   a. defining within a healthcare processing computer a group of related medications dispensed by a pharmacy under said plan, determining within the healthcare processing computer the sales price and group sales percentage of each medication within said group, determining within the healthcare processing computer therefrom a group-weighted sales price for each said medication, and performing within the healthcare processing computer a calculation of a representative price by summing said group-weighted sales prices for all medications within said group;
   b. excluding within the healthcare processing computer from said group and representative price calculation those related medications which have price structures that are not intermediate between higher priced brand name medications and lower priced generic medications within said group;
   c. establishing within the healthcare processing computer a minimum amount at or above said representative price;
   d. for each prescription fulfillment of a medication within said group, paying to said pharmacy an amount equal to the greater of the minimum or said representative price;
   e. the healthcare processing computer periodically repeating step a; and
   f. the healthcare processing computer periodically adjusting said minimum amount of step c.;
   whereby each said pharmacy receives an incentive to preferentially fulfill said prescriptions with lower costs medications with said group when consistent with medical efficacy and prescriber instruction.

2. A method as in claim 1 wherein said representative price comprises an average rate on reimbursement of a pharmacy under said plan.

3. A method as in claim 1 wherein said group comprises at least one each of a branded medication and a generic medication.

4. A method as in claim 1, further comprising excluding within the healthcare processing computer from said group and representative price calculations medications which have been introduced to the market and medications for which the ingredient cost is greater than a normal range of ingredient costs for medications within the group.

5. A method as in claim 1 wherein periodic repetition of step d. occurs on a period determined by a period of overall sales activity of the medications of said group in the marketplace.

6. A method as in claim 5 wherein the period of overall sales activity is two weeks.

7. A method as in claim 1 wherein said periodic assessment of step f. occurs on a period length of not more than one year.

8. A method as in claim 1 further comprising defining within the healthcare processing computer a plurality of groups, each of which is comprised of medications of a single therapeutic class, and conducting steps b. through f. independently for each group, whereby said pharmacy receives different payment of different representative prices for different groups within said plurality, each said representative price being calculated such that said pharmacy has an incentive for each said group to fulfill prescriptions for medications within said group with a lower cost one of said medications.

9. A method as in claim 1 wherein data for steps a. and b. is stored in a healthcare processing computer database comprising medication identifications and current and historical prices and sales amounts for each medication within said database.

10. A method as in claim 4 wherein said exclusion for a newly introduced medication expires one year following the date of its introduction to the market, and thereafter said medication is included within said group.

11. A method as in claim 4 further comprising the healthcare processing computer subsequently reassessing said exclusion of a medication which has a price structure dissimilar to those medications within said group, at such time as there is a change in such price structure, and thereupon terminating said exclusion if such change has occurred and has been sufficient to make the then-current price structure of said medication comparable to price structures of medications already within said group.

12. A method as in claim 1 further comprising the healthcare processing computer step whereby pharmacy performance can be assessed over time according to drug category, prescription dispensing date and/or store with respect to prescription profit sums and averages overall and separately for branded and generic drugs.

* * * * *